(12) United States Patent
Wallner et al.

(10) Patent No.: US 8,252,773 B2
(45) Date of Patent: Aug. 28, 2012

(54) COMBINATION THERAPY WITH ORGANIC ARSENICALS

(75) Inventors: Barbara P. Wallner, Cohasset, MA (US); Philip B. Komarnitsky, Chestnut Hill, MA (US)

(73) Assignee: Ziopharm Oncology, Inc., Boston, MA (US)

( * ) Notice: Subject to any disclaimer, the term of this patent is extended or adjusted under 35 U.S.C. 154(b) by 192 days.

(21) Appl. No.: 12/740,661

(22) PCT Filed: Oct. 31, 2008

(86) PCT No.: PCT/US2008/012385
§ 371 (c)(1),
(2), (4) Date: Jun. 1, 2010

(87) PCT Pub. No.: WO2009/061373
PCT Pub. Date: May 14, 2009

(65) Prior Publication Data
US 2010/0311689 A1 Dec. 9, 2010

Related U.S. Application Data

(60) Provisional application No. 61/001,575, filed on Nov. 2, 2007.

(51) Int. Cl.
*A61K 31/285* (2006.01)
*A61K 31/44* (2006.01)
*A61K 31/513* (2006.01)
*A61K 31/4745* (2006.01)
*A61K 31/573* (2006.01)

(52) U.S. Cl. .......... 514/64; 514/171; 514/274; 514/283; 514/350; 514/504

(58) Field of Classification Search .................... 514/64, 514/171, 274, 283, 350, 504
See application file for complete search history.

(56) References Cited

U.S. PATENT DOCUMENTS

| | | | |
|---|---|---|---|
| 2,349,729 | A | 5/1944 | Hopkinson et al. |
| 6,191,123 | B1 | 2/2001 | Uckun et al. |
| 6,482,815 | B1 | 11/2002 | Uckun et al. |
| 6,482,816 | B1 | 11/2002 | Uckun et al. |
| 6,911,471 | B2 | 6/2005 | Zingaro et al. |
| 6,995,188 | B2 | 2/2006 | Zingaro et al. |
| 7,405,314 | B2 | 7/2008 | Zingaro et al. |
| 7,619,000 | B2 | 11/2009 | Zingaro et al. |
| 2002/0013371 | A1 | 1/2002 | Warrell et al. |
| 2002/0183385 | A1 | 12/2002 | Ellison et al. |
| 2003/0176359 | A1 | 9/2003 | Neuwelt et al. |
| 2004/0028750 | A1 | 2/2004 | Lu |
| 2007/0183972 | A1 | 8/2007 | Gutsch et al. |
| 2008/0139629 | A1 | 6/2008 | Wallner et al. |

FOREIGN PATENT DOCUMENTS

| | | |
|---|---|---|
| EP | 1002537 A1 | 5/2000 |
| SU | 188 971 A | 11/1966 |
| WO | WO-99/24029 A1 | 5/1999 |
| WO | WO-03/057012 | 7/2003 |
| WO | WO-2006/020048 A2 | 2/2006 |
| WO | WO-2007/027344 A2 | 3/2007 |
| WO | WO-2008/054594 A2 | 5/2008 |

OTHER PUBLICATIONS

American Conference of Governmental Industrial Hygienists, Inc. (ACGIH). Arsenic and soluble compounds, including arsine. Documentation of the Threshold Limit Values and Biological Exposure Indices, sixth edition, 1991.
Aslanidis, et al., "Methylarsino-substituted hydroxy carboxylate esters," Chemiker-Zeitung, 112(4):125-127 (1988).
Bachleitner-Hofmann et al., "Arsenic trioxide and ascorbic acid: synergy with potential implications for the treatment of acute myeloid leukaemia," Br. J. Haematol., 112(3):783-786 (2001).
Banks, et al., "Biomolecules Bearing the S- or SeAsMe2 Function: Amino Acid and Steroid Derivatives," Jr. of Medicinal Chemistry, American Chemical Society, 22(5):572-575 (1979).
Barber, Harry J., "Hydrolysis of arylthioarsinites Hydrolysis of arylthioarsinites," Jr. of the Chemical Society, Abstracts 1365-9 (1932).
Beckermann, "Determination of monovethylarsonic acid and dimethylarsinic acid by derivatization with thioglycolic acid methyl ester and gas-liquid chromatographic separation," Analytica Chimica Acta, 135(1):77-84 (1982).
Beliles, "The Metals," In *Patty's Industrial Hygiene and Toxicology, fourth edition* G.D. Clayton and F.E. Clayton, eds. John Wiley & Sons, Inc.: New York. pp. 1913-1925 (1994).
Caira, M.R., "Crystalline Polymorphism of Organic Compounds," Topics in Current Chemistry, 198:163-208 (1998).
Calleja and Warrell, "Differentiating agents in pediatric malignancies: all-trans-retinoic acid and arsenic in acute promyelocytic leukemia," Curr. Oncol. Rep., 2:519-523 (2000).
Chen, et al., "6-thio-and-seleno-alpha-D-glucose esters of dimethylarsinous acid," Carb. Res. 50:53-62 (1976).
Chen, et al., "Synthesis of 1- and 6-S and 1- and 6-Se-derivatives of 2-amino-2-deoxy-alpha/beta-D-glucopyrasone," J. Chemical Soc, Perkin Trans., 1:2287-2293 (1980).
Cullen, et al., "The metabolism of methylarsine oxide and sulfide," Applied Organometallic Chemistry, 3(1):71-78 (1989).
Cullen, et al., "The reaction of methylarsenicals with thiols: some biological implications," Journal of Inorganic Biochemistry, 21(3):179-194 (1984).

(Continued)

*Primary Examiner* — Raymond Henley, III
(74) *Attorney, Agent, or Firm* — Wilmer Cutler Pickering Hale and Dorr LLP (57) ABSTRACT

The invention provides a combination therapy wherein one or more other therapeutic agents are administered with an organic arsenical, preferably SGLU-1 or a pharmaceutically acceptable salt thereof. The invention also relates to methods for the treatment of cancer, comprising administering SGLU-1 in combination with another therapeutic agent. Another aspect of the invention relates to a kit comprising SGLU-1 and another therapeutic agent.

15 Claims, 10 Drawing Sheets

OTHER PUBLICATIONS

Cuzick, et al., "Medicinal arsenic and internal malignancies," Br. J. Cancer, 45:904-911 (1982).

Daniel, et al., "Dimethylarsinous Acid Esters of 1-Thio- and -Selenogalactose, A New Class of Potential Carcinostatic Agents," Phosphorus and Sulfur, 4:179-185 (1978).

Emran, et al., "Synthesis and biodistribution of radioarsenic labeled dimethylarsinothiols: derivatives of pennicillamine and mercaptoethanol," International Journal of Nuclear Medicine and Biology, 11(3-4):259-261 (1984).

Fatouros, et al., "Preparation and properties of arsonolipid containing liposomes," Chemistry and Physics of Lipids, 109:75-89 (2001).

Forkner and McNair-Scott, "Arsenic as a therapeutic agent in chronic myeloid leukemia," JAMA, 97(1):3-6 (1931).

Geissler, et al., "In vivo effects of arsenic trioxide in refractory acute myeloid leukemia other than acute promyelocytic leukemia," Blood, 94:4230a (1999).

Gillard, et al., "Amylo-1,6-glucosidase/4-α-glucanotransferase," The Journal of Biological Chemistry, 255(18): 8451-8457 (1980).

Goyer, "Toxic effects of metals" In *Casarett and Doull's Toxicology: The Basic Science of Poisons*, 5th edition. C.D. Klassen, ed. McGraw-Hill: New York, pp. 691-698 (1996).

Grignani, et al., "The acute promyelocytic leukemia-specific PML-RAR alpha fusion protein inhibits differentiation and promotes survival of myeloid precursor cells," Cell, 74:423-431 (1993).

Hughes and Kenyon, "Dose-dependent effects on the disposition of monomethylarsonic acid and dimethylarsinic acid in the mouse after intravenous administration," J. Toxicol. Environ. Health, 53(2):95-112 (1998).

IARC. Some metals and metallic compounds. IARC Monographs on the Evaluation of the Carcinogenic Risk of Chemicals to Man. vol. 23:39-141 (1980).

Ionov, et al., "Reaction of tertiary arsine sulfides with alkyl chlorocarbonates," Zhurnal Obshchei Khimii, 46(11):2555-2558 (1976).

Kala, et al., "The MRP2/cMOAT transporter and arsenic-glutathione complex formation are required for bilary excretion of arsenic," J. Biol. Chem., 275(43):33404-33408 (2000).

King and Ludford, "Relation between the constitution of arsenicals and their action on cell division," Journal of the Chemical Society Abstracts, 2086-2088 (1950).

Kitamura, et al., "New retinoids and arsenic compounds for the treatment of refractory acute promyelocytic leukemia: clinical and basic studies for the next generation," Cancer Chemother Pharmacol., 40 (Suppl):S36-S41 (1997).

Knock, et al., "The use of selected sulfhydryl inhibitors in a preferential drug attack on cancer," Surg. Gynecol. Obstet., 133:458-466 (1971).

Kober, et al., "Reaction of (dimethylamino)dimethylarsine with 1, 2-diols Reaction of (dimethylamino)dimethylarsine with 1, 2-diols," Zeitschrift Fuer Anorganische Und Allgemeine Chemie, 406(1):52-61 (1974).

Konig, A., et al., "Comparative activity of melarsoprol and arsenic trioxide in chronic B-cell leukemia lines," Blood 90:562-570 (1997).

Lallemand-Breitenbach, et al., "Retinoic acid and arsenic synergize to eradicate leukemic cells in a mouse model of acute promyelocytic leukemia," J. Exp. Med., 189:1043-1052 (1999).

Lam, et al., "Spectroscopic studies of arsenic (III) binding to *Escherichia coli* RI methyltransferase and to two mutants, C223S and W183F," Biochemistry, 31(43):10438-10442 (1992).

Lin, et al., "Methylarsenicals and arsinothiols are potent inhibitors of mouse liver thioredoxin reductase," Chemical Research in Toxicology, 12(10):924-930 (1999).

Mandic et al., "Tumor angiogenesis and endometrial cancer," Archive of Oncology, 10(2):79-81 (2002).

Mester, et al., "Speciation of dimethylarsinic acid and monomethylarsonic acid by gas chromatography-mass spectrometry," Jr. of Chromatography, 832(1+2):183-190 (1999).

Mountain, et al., "Chemotherapy Studies in an Animal Tumor Spectrum: III. Evaluation of the Toxicity Differentil Index," Cancer Res., 26:258-264 (1966).

Rivi, et al., "Organic arsenical melarsoprol shows growth suppressive activity via programmed cell death on myeloid and lymphoid leukemia derived cell lines," Blood (Suppl), 88:68a (1996).

Rosenthal, et al., "The Synthesis and Characterization of Thio Sugar Esters of Diorganylarsinous Acids," Phosphorus and Sulfur, 9:107-116 (1980).

Rousselot, et al., "Use of arsenic trioxide (As2O3) in the treatment of chronic myelogenous leukemia: in vitro and in vivo studies," Blood, 94:4457a (1999).

Schoene, et al., "Speciation of arsenic-containing chemical warfare agents by gas chromatographic analysis after derivatization with thioglcolic acid methyl ester," Journal of Chromatography, 605(2):257-262 (1992).

Scott, et al., "Reactions of arsenic (III) and arsenic (V) species with glutathione," Chemical Research in Toxicology, 6(1):102-106 (1993).

Soignet, et al., "Clinical study of an organic arsenic melarsoprol, in patients with advanced leukemia," Cancer Chemother. Pharmacol. 44:417-421 (1999).

Soignet, et al., "Dose-ranging and clinical pharmacologic study of arsenic trioxide in patients with advanced hematologic cancers," Blood, 94:1247a (1999).

Styblo, et al., "Comparative inhibition of yeast glutathione reductase by arsenicals and arsenothiols," Chemical Research in Toxicology, 10(1):27-33 (1997).

Tallman, "Therapy of acute promyelocytic leukemia: all-tans retinoic acid and beyond," Leukemia, 12 (Suppl 1):S37-S40 (1998).

Tsalev, et al., "Flow-injection hydride generation atomic absorption spectrometric study of the automated on-line pre-reduction of arsenate, methylarsonate and dimethylarsinate and high-performance liquid chromatographic separation of their I-cysteine complexes," Talanta, 51(6):1059-1068 (2000).

Tsao, et al., "Optically Detected Magnetic Resonance Study of the Interaction of an Arsenic(III) Derivative of Cacodylic Acid with EcoRI Methyl Transferase," Biochemistry, 30(18):4565-72 (1991).

Vega, et al., "Differential effects of trivalent and pentavalent arsenicals on cell proliferation and cytokine secretion in normal human epiderman keratinocytes," Toxicology and Applied Pharmacology, 172(3):225-232 (2001).

West, Anthony R., "Solid State Chemistry and Its Applications," Wiley, New York pp. 358 and 365 (1988).

Wiernik, et al., "Phase II trial of arsenic trioxide ($As_2O_3$) in patients with relapsed/refractory acute myeloid leukemia, blast crisis of CML or myelodysplasia," Blood, 94:2283a (1999).

Zhang, et al., "Arsenic trioxide treated 72 cases of acute promyelocytic leukemia," Chin. J. Hematol., 17:58-62 (1996).

Zingaro et al., "Thio and Seleno Sugar Esters of Dialkylarsinous Acids," Carbohydrate Research, 29:147-152 (1973).

Zingaro, Ralph A., "Seleno and Thio Sugar Esters of Group VA Acids," Chemica Scripta, 8A: 51-57 (1975).

Written Opinion and International Search Report for PCT/US2008/012385 mailed Mar. 31, 2009.

Hirano S. et al., "Cytotoxic effects of S-(dimethylarsino)-glutathione: a putative intermediate metabolite of inorganic arsenicals," Toxicology. Oct. 3, 2006 (Epub. Jul. 14, 2006), 227(1-2):45-52.

Sakurai T. et al., "Toxicity of a trivalent organic arsenic compound, dimethylarsinous glutathione in a rat liver cell line (TRL 1215)," Br J Pharmacol. Dec. 2006 (Epub. Oct. 16, 2006), 149(7):888-897.

Craig et al.: "Phase II trial of darinaparsin in leukemias and lymphomas," AACR Meeting Abstracts Online, Apr. 2008, XP000002657429, Retrieved from the Internet: URL:http://www.aacrmeetingabstracts.org/cgi/content/meeting_abstract/2008/1_Annual_Meeting/5527?maxtoshow=&hits=10&RESULTFORMAT=&author1=craig&andorexactfulltext=and&searchid=1&FIRSTINDEX=0&sortspec=relevance&resourcetype=HWCIT [retrieved on Aug. 22, 2011] (2 pages).

COMBINATION THERAPY WITH ORGANIC ARSENICALS

RELATED APPLICATIONS

This application is a national stage filing under 35 U.S.C. §371 of International Application No. PCT/US2008/012385, filed Oct. 31, 2008, which claims the benefit of priority to U.S. Provisional Application No. 61/001,575 filed Nov. 2, 2007, the contents of which are incorporated by reference in their entirety. International Application No. PCT/US2008/012385 was published under PCT Article 21(2) in English.

BACKGROUND OF THE INVENTION

Arsenic trioxide, an inorganic compound, has been approved for the treatment of patients with relapsed or refractory acute promyelocytic leukemia (APL) and is being evaluated as therapy for other leukemia types. Preliminary data and recent experience in the U.S., however, suggest a role for arsenic trioxide in the other hematologic cancers as well. Consequently, the activity of arsenic trioxide as an anti-leukemic agent is currently being investigated in many types of leukemia. Although the results look favorable in terms of the response rate of some of the leukemia types that are being investigated, systemic toxicity of arsenic trioxide is a problem (Soignet et al., 1999; Wiernik et al., 1999; Geissler et al., 1999; Rousselot et al., 1999).

S-dimethylarsino-glutathione (SGLU-1) has a multifaceted mechanism of action mediated by disrupted mitochondrial function, increased reactive oxygen species (ROS) production, modified signal transduction, and anti-angiogenesis and has been shown to be active against multiple in vitro and animal cancer models.

SUMMARY OF THE INVENTION

One aspect of the invention provides a combination therapy wherein one or more other therapeutic agents are administered with an organic arsenical, preferably SGLU-1, shown below or a pharmaceutically acceptable salt thereof Such combination treatment may be achieved by way of the simultaneous, sequential, or separate dosing of the individual components of the treatment.

In certain embodiments, the invention relates to methods for the treatment of cancer, comprising administering SGLU-1 in combination with another therapeutic agent. In certain embodiments, the cancer is selected from brain, lung, liver, spleen, kidney, lymph node, small intestine, pancreas, blood cells, bone, colon, stomach, breast, endometrium, prostate, testicle, ovary, central nervous system, skin, head and neck, esophagus, and bone marrow cancer.

Another aspect of the invention relates to a kit comprising SGLU-1 and another therapeutic agent.

DETAILED DESCRIPTION OF THE INVENTION

One aspect of the invention provides a combination therapy wherein one or more other therapeutic agents are administered with an organic arsenical, preferably SGLU-1, shown below Such combination treatment may be achieved by way of the simultaneous, sequential, or separate dosing of the individual components of the treatment. Such a combination may be synergistic (effect elicited by combination exceeds expected sum of effects elicited by individual drugs) or additive (effect elicited by combination equals the sum of the effects by individual drugs).

In certain embodiments, SGLU-1 is administered in combination with another therapeutic agent selected from bortezomib, melphalan, dexamethasone, irinotecan, oxaliplatin, 5-fluorouracil, doxorubicin, and sorafenib. In certain embodiments, the other therapeutic agent is selected from bortezomib, dexamethasone, irinotecan, oxaliplatin, and sorafenib, preferably bortezomib. In certain such embodiments, the combination is synergistic. In certain alternative embodiments, the combination is additive.

In certain embodiments, SGLU-1 is administered in combination with another therapeutic agent such that the combination is synergistic. In certain such embodiments, the other therapeutic agent is selected from bortezomib and oxaliplatin.

In certain embodiments, SGLU-1 is administered in combination with another therapeutic agent such that the combination is additive. In certain such embodiments, the other therapeutic agent is selected from dexamethasone, irinotecan, and sorafenib.

Another aspect of the invention relates to methods for the treatment of cancer, comprising administering SGLU-1 in combination with another therapeutic agent. In certain such embodiments, the invention relates to methods for the treatment of a cancer selected from brain, lung, liver, spleen, kidney, lymph node, small intestine, pancreas, blood cells, bone, colon, stomach, breast, endometrium, prostate, testicle, ovary, central nervous system, skin, head and neck, esophagus, and bone marrow cancer. In certain such embodiments, the cancer is a hematological cancer.

In certain embodiments, the cancer is selected from leukemia, lymphoma, multiple myeloma, myelodysplasia, myeloproliferative disease, and refractory leukemia. In certain such embodiments, the cancer is acute promyelocytic leukemia.

In certain embodiments, the cancer is selected from multiple myeloma, colon, and hepatocellular carcinoma.

As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e., not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

Another aspect of the invention relates to a kit, comprising SGLU-1 and another therapeutic agent. In certain embodiments, the other therapeutic agent is selected from bortezomib, melphalan, dexamethasone, irinotecan, oxaliplatin, 5-fluorouracil, doxorubicin, and sorafenib.

Administration of the SGLU-1 may precede or follow the other therapeutic agent by intervals ranging from minutes to days. In certain such embodiments, the SGLU-1 and the other therapeutic agent may be administered within about 1 minute, about 5 minutes, about 10 minutes, about 30 minutes, about 60 minutes, about 2 hours, about 4 hours, about 6 hours, 8 hours, about 10 hours, about 12 hours, about 18 hours, about 24 hours, about 36 hours, or even about 48 hours or more of one another. Preferably administration of the SGLU-1 and the other therapeutic agent will be within about 1 minute, about 5 minutes, about 30 minutes, or even about 60 minutes of one another.

In certain embodiments, the SGLU-1 and the other therapeutic agent may be administered according to different dosing regimen (e.g., the SGLU-1, for example may be administered once a day while the other therapeutic agent may be administered only once every three weeks) such that in some instances administration of the SGLU-1 and the other therapeutic agent will be within about 60 minutes of one another, while in other instances, administration of the SGLU-1 and the other therapeutic agent will be within days or even weeks of one another.

In certain embodiments, SGLU-1 is provided as a formulation further comprising a pharmaceutical carrier, wherein the formulation has a pH of 5 to 8, or even 5 to 7.

Compounds described herein can be administered in various forms, depending on the disorder to be treated and the age, condition, and body weight of the patient, as is well known in the art. For example, where the compounds are to be administered orally, they may be formulated as tablets, capsules, granules, powders, or syrups; or for parenteral administration, they may be formulated as injections (intravenous, intramuscular, or subcutaneous), or drop infusion preparations. These formulations can be prepared by conventional means, and if desired, the active ingredient may be mixed with any conventional additive or excipient, such as a binder, a disintegrating agent, a lubricant, a corrigent, a solubilizing agent, a suspension aid, an emulsifying agent, a coating agent, a cyclodextrin, and/or a buffer. The dosage will vary depending on the symptoms, age and body weight of the patient, the nature and severity of the disorder to be treated or prevented, the route of administration and the form of the drug. The amount of active ingredient which can be combined with a carrier material to produce a single dosage form will generally be that amount of the compound which produces a therapeutic effect.

In certain embodiments, the SGLU-1 and the other therapeutic agent may be in the same form (e.g., both may be administered as tablets or both may be administered intravenously) while in certain alternative embodiments, the SGLU-1 and the other therapeutic agent may be in different forms (e.g. one may be administered as a tablet while the other is administered intravenously).

The precise time of administration and/or amount of the composition that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage, and type of medication), route of administration, etc. However, the above guidelines can be used as the basis for fine-tuning the treatment, e.g., determining the optimum time and/or amount of administration, which will require no more than routine experimentation consisting of monitoring the subject and adjusting the dosage and/or timing.

The phrase "pharmaceutically acceptable" is employed herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition, or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose, and sucrose; (2) starches, such as corn starch, potato starch, and substituted or unsubstituted β-cyclodextrin; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions of the present invention are non-pyrogenic, i.e., do not induce significant temperature elevations when administered to a patient.

The term "pharmaceutically acceptable salt" refers to the relatively non-toxic, inorganic and organic acid addition salts of the inhibitor(s). These salts can be prepared in situ during the final isolation and purification of the inhibitor(s), or by separately reacting a purified inhibitor(s) in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. (See, for example, Berge et al. (1977) "Pharmaceutical Salts", *J. Pharm. Sci.* 66: 1-19.)

In other cases, the inhibitors useful in the methods of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic inorganic and organic base addition salts of an inhibitor(s). These salts can likewise be prepared in situ during the final isolation and purification of the inhibitor(s), or by separately reacting the purified inhibitor(s) in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethyl amine, diethylamine, ethylenediamine, ethanolamine, diethanolamine, piperazine, and the like (see, for example, Berge et al., supra).

Wetting agents, emulsifiers, and lubricants, such as sodium lauryl sulfate and magnesium stearate, as well as coloring agents, release agents, coating agents, sweetening, flavoring, and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert matrix, such as gelatin and glycerin, or sucrose and acacia) and/or as mouthwashes, and the like, each containing a predetermined amount of an inhibitor(s) as an active ingredient. A composition may also be administered as a bolus, electuary, or paste.

In solid dosage forms for oral administration (capsules, tablets, pills, dragees, powders, granules, and the like), the active ingredient is mixed with one or more pharmaceutically acceptable carriers, such as sodium citrate or dicalcium phosphate, and/or any of the following: (1) fillers or extenders, such as starches, cyclodextrins, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets, and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols, and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered inhibitor(s) moistened with an inert liquid diluent.

Tablets, and other solid dosage forms, such as dragees, capsules, pills, and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes, and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes.

The active ingredient can also be in micro-encapsulated form, if appropriate, with one or more of the above-described excipients.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents, and emulsifiers such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof.

Besides inert diluents, the oral compositions can also include adjuvants such as wetting agents, emulsifying and suspending agents, sweetening, flavoring, coloring, perfuming, and preservative agents.

Suspensions, in addition to the active inhibitor(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions of this invention suitable for parenteral administration comprise one or more inhibitors(s) in combination with one or more pharmaceutically acceptable sterile aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include tonicity-adjusting agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. For example, delayed absorption of a parenterally administered drug form is accomplished by dissolving or suspending the drug in an oil vehicle.

Injectable depot forms are made by forming microencapsule matrices of inhibitor(s) in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection, and infusion.

The phrases "systemic administration," "administered systemically," "peripheral administration" and "administered peripherally" as used herein mean the administration of a ligand, drug, or other material other than directly into the central nervous system, such that it enters the patient's system and thus, is subject to metabolism and other like processes, for example, subcutaneous administration.

Administration of the therapeutic compositions of the present invention to a patient will follow general protocols for the administration of chemotherapeutics, taking into account the toxicity, if any. It is expected that the treatment cycles would be repeated as necessary. It also is contemplated that various standard therapies or adjunct cancer therapies, as well as surgical intervention, may be applied in combination with the described arsenical agent.

Regardless of the route of administration selected, the inhibitor(s), which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

EXAMPLES

Example 1

Figure 1:
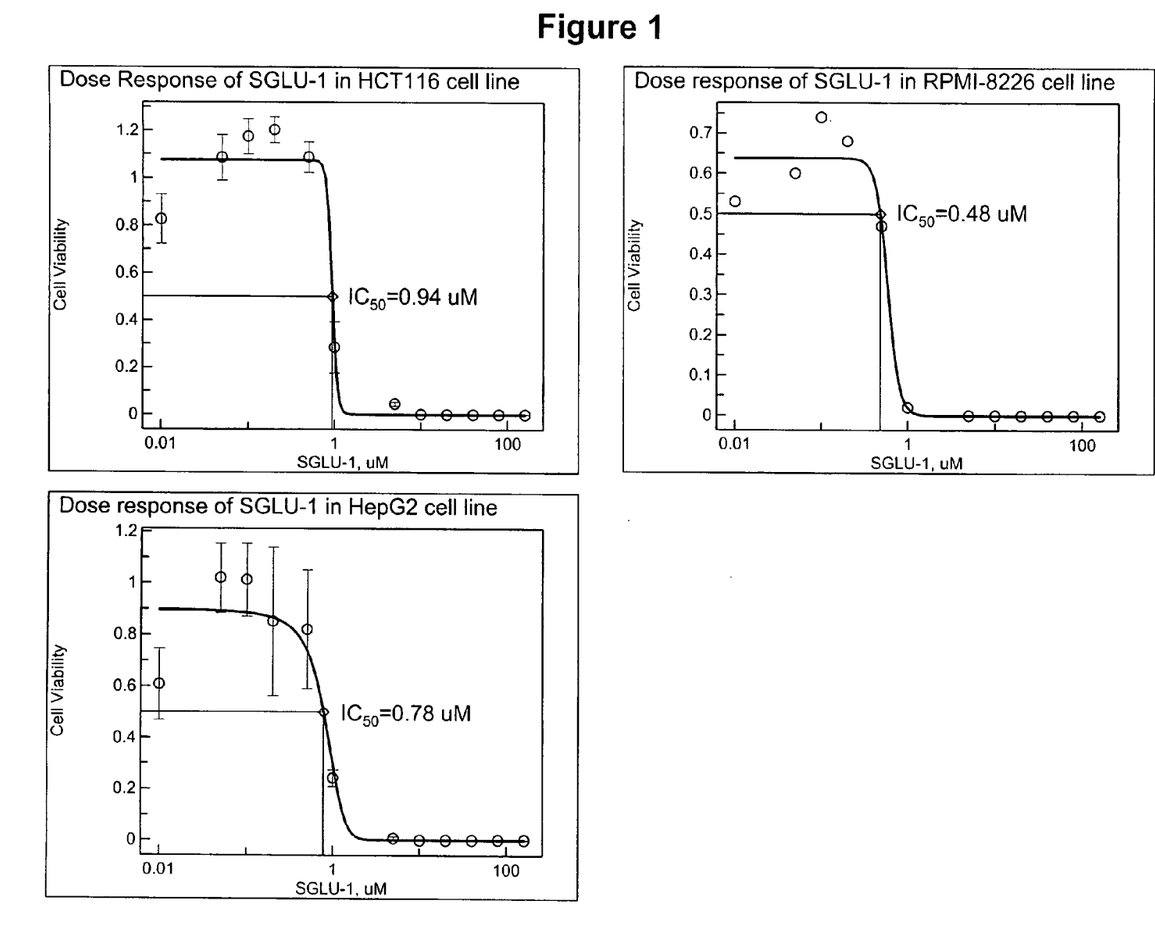
FIG. 1 shows dose response of SGLU-1 single agent in HCT116 colon carcinoma, RPMI 8226 multiple myeloma and HepG2 hepatocellular carcinoma cell lines
Figure 2:
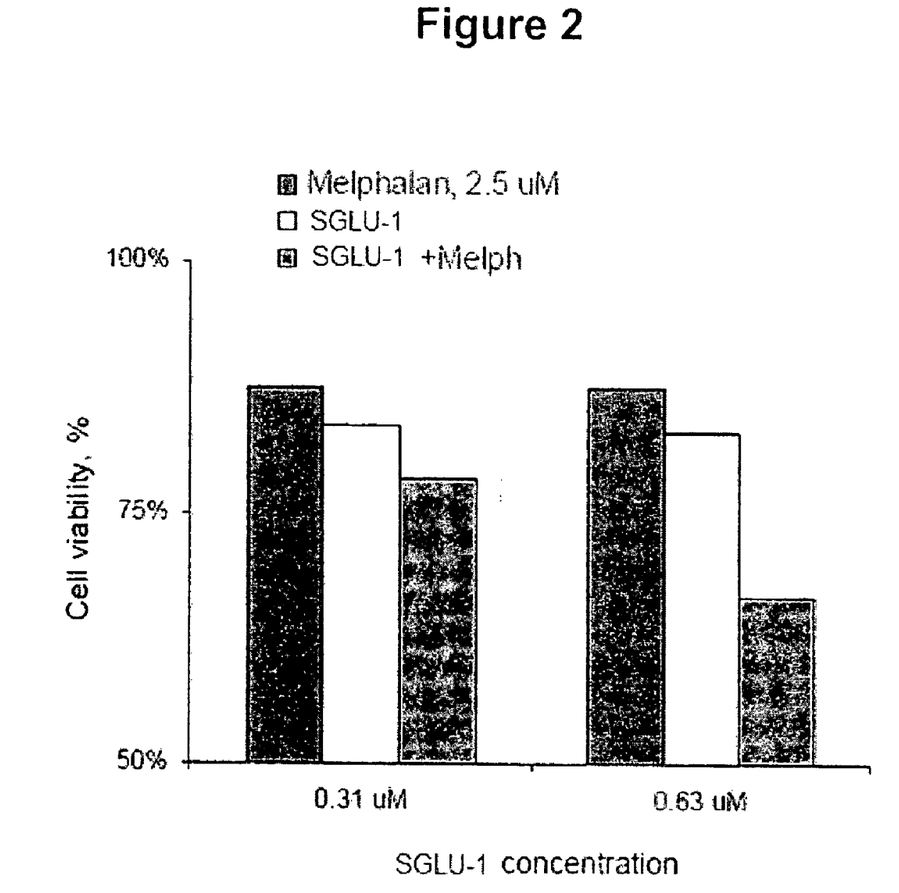
FIG. 2 shows percent viability vs. vehicle control of RPMI 8226 cells incubated in the presence of melphalan (2.5 µM) and SGLU-1 (0.31 and 0.63 µM) combination and single agents as described in the example 2.
Figure 3:
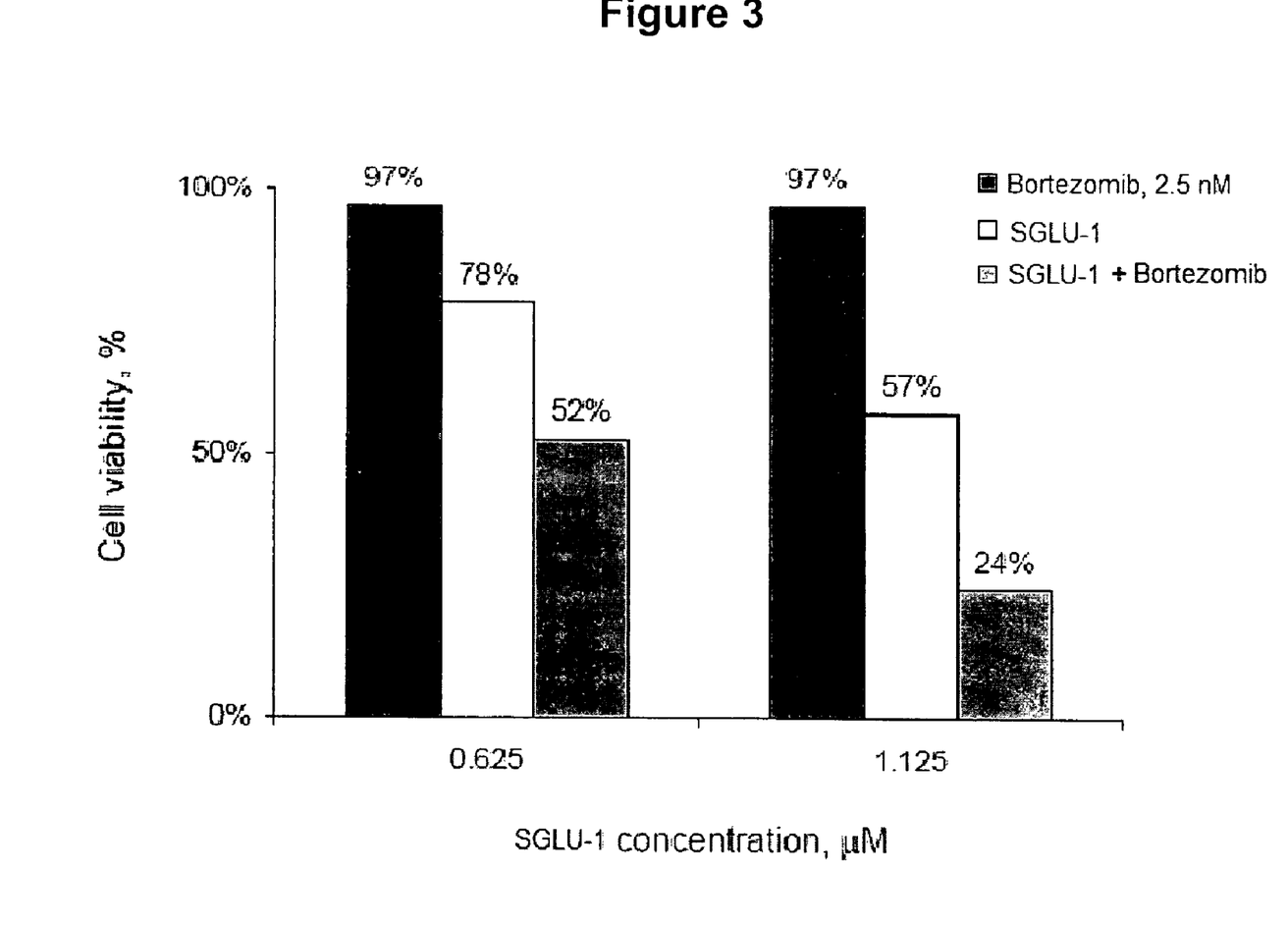
FIG. 3 shows % viability vs. vehicle control of RPMI 8226 cells incubated in the presence of bortezomib (2.5 nM) and SGLU-1 (0.625 and 1.125 µM) combination and single agents as described in the example 2.
Figure 4:
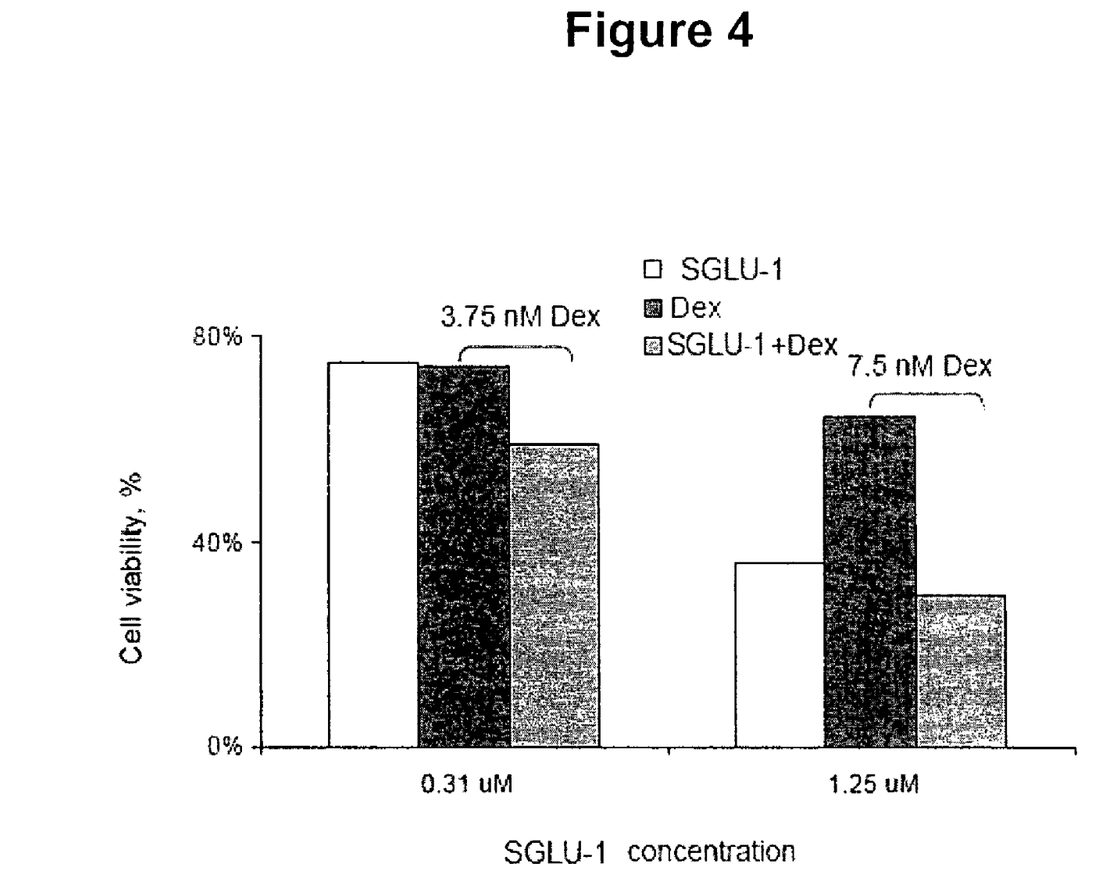
FIG. 4 shows % viability vs. vehicle control of RPMI 8226 cells incubated in the presence of dexamethasone (3.75 and 7.5 nM) and SGLU-1 (0.31 and 1.25 µM) combination and single agents as described in the example 2.
Figure 5:
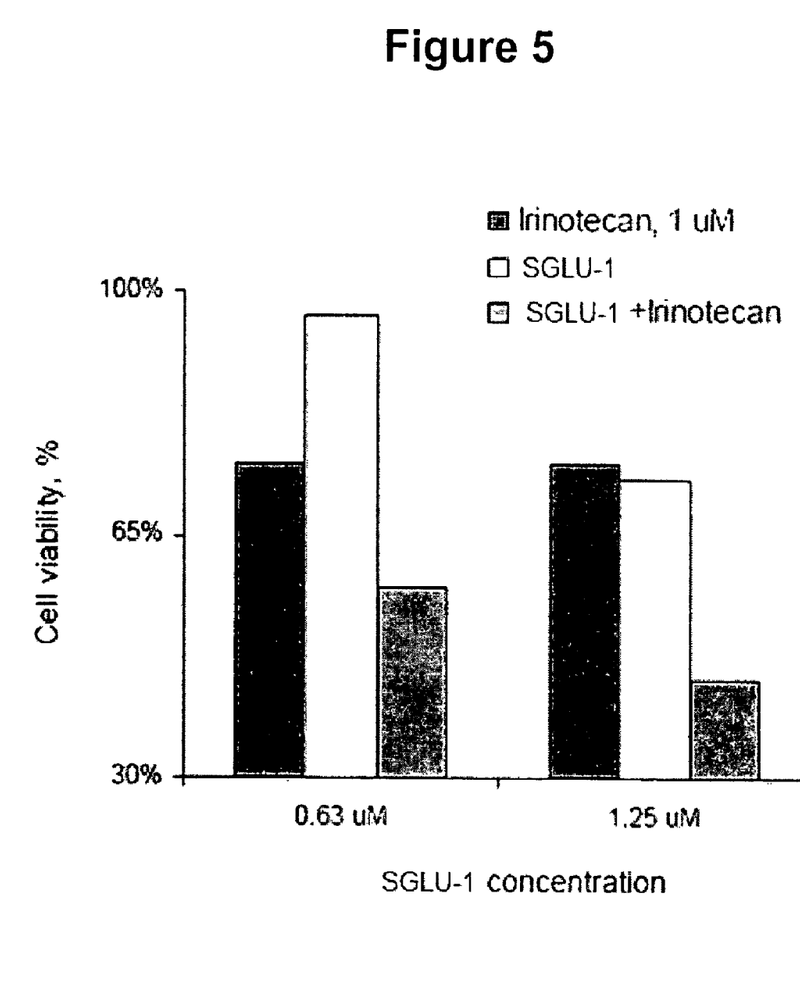
FIG. 5 shows % viability vs. vehicle control of HCT116 cells incubated in the presence of irinotecan (1 µM) and SGLU-1 (0.63 and 1.25 µM) combination and single agents as described in the example 2.
Figure 6:
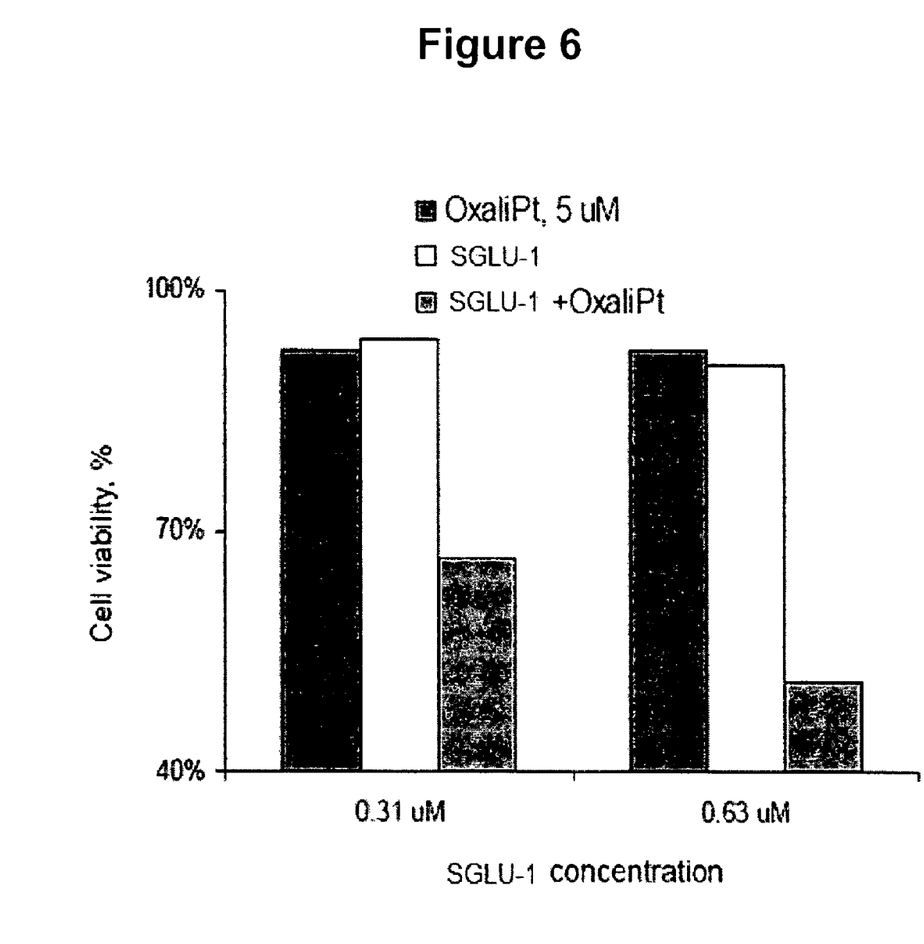
FIG. 6 shows % viability vs. vehicle control of HCT116 cells incubated in the presence of oxaliplatin (5 µM) and SGLU-1 (0.31 and 0.63 µM) combination and single agents as described in the example 2.
Figure 7:
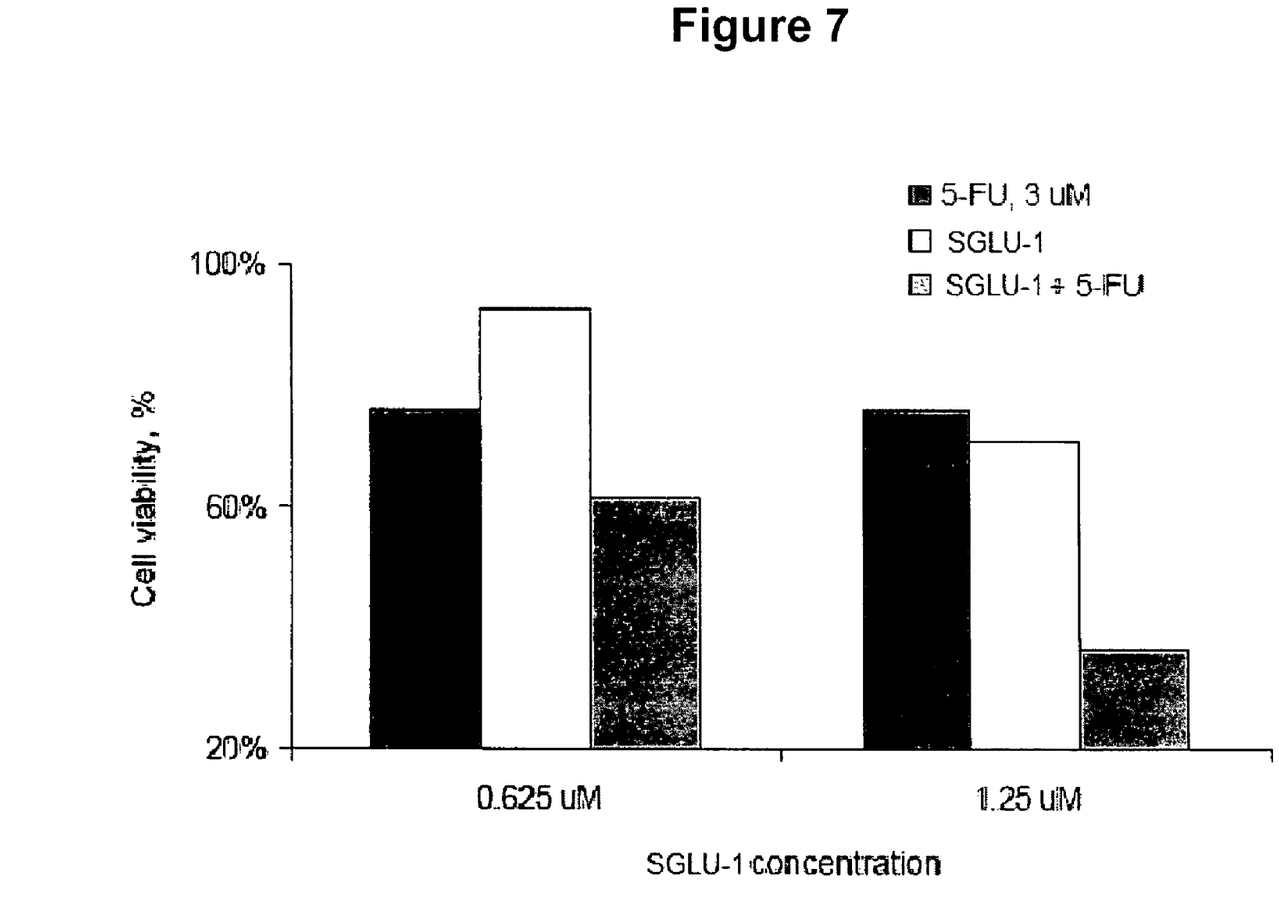
FIG. 7 shows % viability vs. vehicle control of HCT116 cells incubated in the presence of 5-fluorouracil (3 µM) and SGLU-1 (0.625 and 1.25 µM) combination and single agents as described in the example 2.
Figure 8:
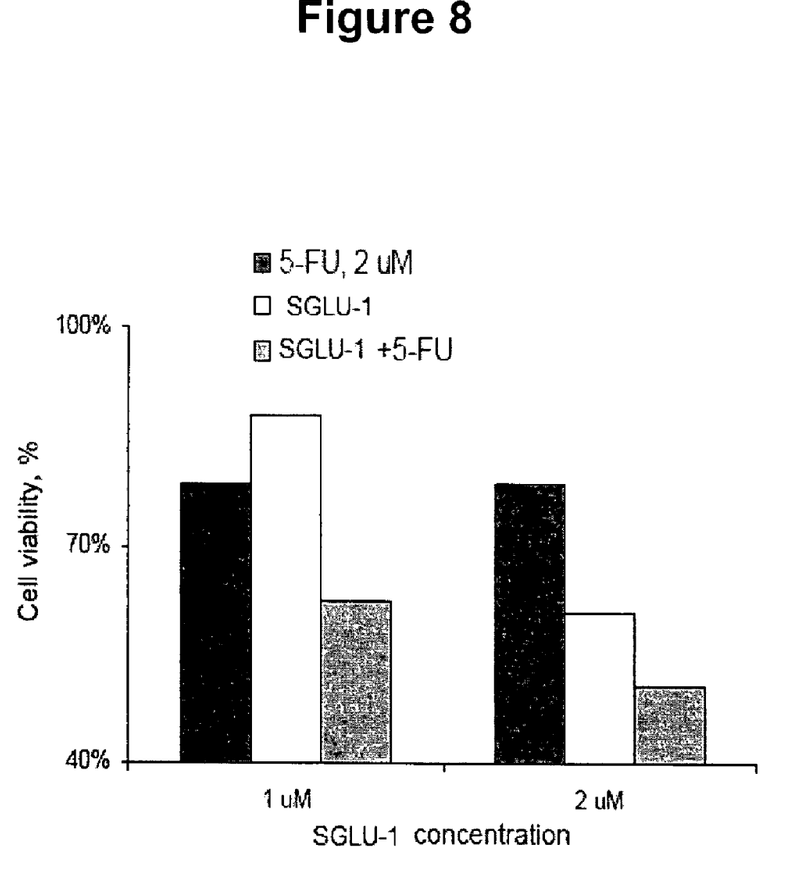
FIG. 8 shows % viability vs. vehicle control of HepG2 cells incubated in the presence of 5-fluorouracil (2 µM) and SGLU-1 (1 and 2 µM) combination and single agents as described in the example 2.
Figure 9:
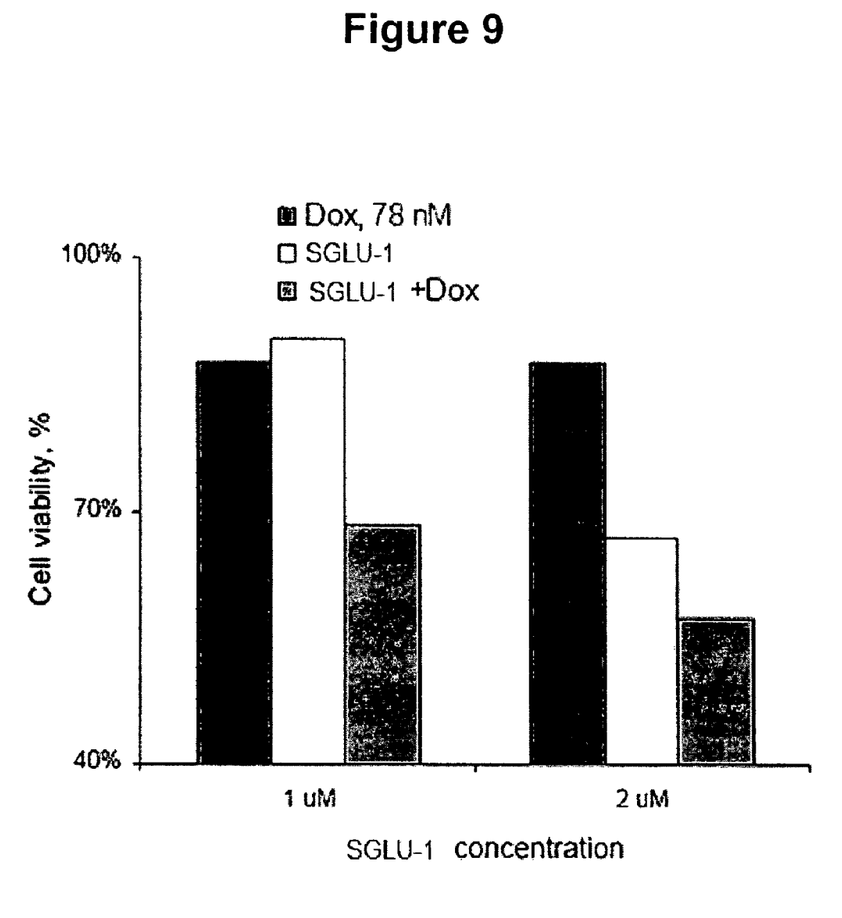
FIG. 9 shows % viability vs. vehicle control of HepG2 cells incubated in the presence of doxorubicin (78 nM) and SGLU-1 (1 and 2 µM) combination and single agents as described in the example 2.
Figure 10:
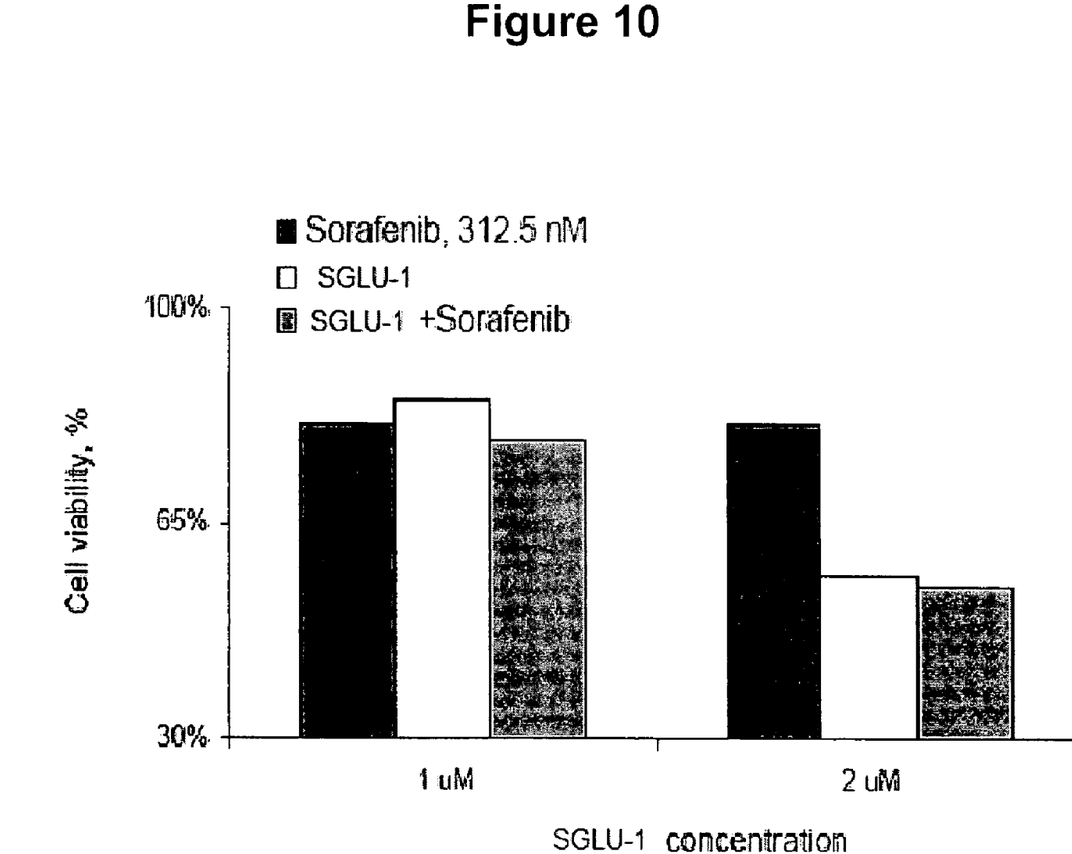
FIG. 10 shows % viability vs. vehicle control of HepG2 cells incubated in the presence of sorafenib (312.5 nM) and SGLU-1 (1 and 2 µM) combination and single agents as described in the example 2.

The cytotoxic effects of SGLU-1, bortezomib, dexamethasone, doxorubicin, melphalan, 5-fluorouracil, irinotecan, sorafenib and oxaliplatin single agents were determined in the respective cell lines using the CellTiter-Glo (Promega) assay (FIG. 1 for SGLU-1 and data not shown for other single agents). Data points were fitted using XLfit software package, and $IC_{50}$ values for single agents determined. Based on the $IC_{50}$ values concentration ranges were selected for the combination part of the study.

Experimental setup: RPMI-8226 cells were cultured in RPMI-1640 supplemented with 2 mM glutamine dipeptide, 10 mM HEPES, 1 mM sodium pyruvate, and 10% fetal bovine serum (FBS). HepG2 and HCT116 cells were cultured in RPMI-1640 supplemented with 2 mM glutamine dipeptide, and 10% FBS. Stock solutions of all compounds, with the exception of bortezomib and SGLU-1, were prepared in DMSO. Stock solution concentrations were such that the highest concentration of DMSO did not exceed 1% when the compounds were added to cell culture. Bortezomib was reconstituted in saline according to the manufacturer's instructions, and SGLU-1 was reconstituted in the appropriate culture medium.

RPMI 8226 cells were seeded at 10,000 cells/well, while HepG2 and HCT116 cells were seeded at 5,000 cells/well in

96-well plates and incubated overnight in a 37° C., 5% $CO_2$ cell culture incubator. 24 hr after seeding, all compounds were added to the appropriate wells. Cells were exposed to compounds for 72 hr. CellTiter-Glo assays were carried out according to manufacturer instructions.

Example 2

The results from Example 1 were used to select the concentration ranges of each compound for the combination studies with SGLU-1 in order to investigate any synergistic or additive interaction. Two-dimensional serial dilution concentration matrix 96-well plates were set up with each well containing unique combination of concentrations of test agents (prototype matrix plate setup shown in Table 1). As seen in FIGS. 2 to 10, additive and synergistic effects were observed.

The invention claimed is:

1. A method for treating cancer, comprising administering a compound having a structure of formula (I)

(I)

or a pharmaceutically acceptable salt thereof; and

TABLE 1

| | | \multicolumn{10}{c}{$2^{nd}$ Test Agent two-fold serial dilutions →} |
| | | 1 | 2 | 3 | 4 | 5 | 6 | 7 | 8 | 9 | 10 |
|---|---|---|---|---|---|---|---|---|---|---|---|
| | A | $2 \times IC_{50}$ | $IC_{50}$ | $0.5 \times IC_{50}$ | $0.25 \times IC_{50}$ | $0.125 \times IC_{50}$ | $0.063 \times IC_{50}$ | $0.031 \times IC_{50}$ | $0.016 \times IC_{50}$ | $0.0078 \times IC_{50}$ | 0 |
| | B | $IC_{50}$ | | | | | | | | | |
| SGLU-1 two-fold serial dilutions | C | $0.5 \times IC_{50}$ | | | | | | | | | |
| | D | $0.25 \times IC_{50}$ | | | | | | | | | |
| | E | $0.125 \times IC_{50}$ | | | | | | | | | |
| | F | $0.063 \times IC_{50}$ | | | | | | | | | |
| | G | $0.031 \times IC_{50}$ | | | | | | | | | |
| ↓ | H | 0 | | | | | | | | | |

☐ - Wells with combination of two agents

▨ - Wells with SGLU-1 single agent

▦ - Wells with $2^{nd}$ test drug agent

▦ - Wells with no test agents added

Experimental setup: for the SGLU-1 drug combination assays, RPMI-8226 cells were seeded in 96 well plates at 10,000 cells/well. HepG2 and HCT116 cells were seeded in 96 well plates at 5,000 cells/well. Plates were incubated overnight in a 37° C., 5% $CO_2$ cell culture incubator. Test compounds were added 24 hr after seeding. Stock solutions of all agents were prepared as described in Example 1. SGLU-1 was made fresh from powdered stocks for each assay. Once in culture medium it was kept on ice for no longer than 1 hr before addition to the cells. Cells were exposed to the drug combinations for 72 hr, at which time the CellTiter-Glo (Promega) assays were carried out according to manufacturer instructions to determine number of viable cells.

All publications and patents cited herein are hereby incorporated by reference in their entirety.

Those skilled in the art will recognize, or be able to ascertain using no more than routine experimentation, many equivalents to the specific embodiments of the invention described herein. Such equivalents are intended to be encompassed by the following claims.

one or more other therapeutic agents selected from bortezomib, dexamethasone, irinotecan, oxaliplatin, 5-fluorouracil, and sorafenib;

wherein the cancer is selected from leukemia, lymphoma, multiple myeloma, myelodysplasia, myeloproliferative disease, refractory leukemia, promyelocytic leukemia, acute promyelocytic leukemia, hematological cancer, brain, lung, liver, spleen, kidney, lymph node, small intestine, pancreas, blood cells, bone, colon, stomach, breast, endometrium, prostate, testicle, ovary, central nervous system, skin, head and neck, esophagus, bone marrow cancer and hepatocellular carcinoma.

2. A method of claim 1, wherein the compound is provided as a formulation further comprising a pharmaceutical carrier, wherein the formulation has a pH of 5 to 7.

3. A method of claim 1 or 2, wherein the compound is administered orally.

4. A method of claim 1 or 2, wherein the compound is administered intravenously.

5. A method of claim 1, wherein the compound and the one or more other therapeutic agents together are synergistic.

6. A method of claim 1, wherein the one or more other therapeutic agents are selected from bortezomib and oxaliplatin.

7. A method of claim 1, wherein the therapeutic effect of the compound and the one or more other therapeutic agents together are additive.

8. A method of claim 1, wherein the one or more other therapeutic agent is selected from dexamethasone, irinotecan, 5-fluorouracil, and sorafenib.

9. A method of claim 1, wherein the cancer is selected from brain, lung, liver, spleen, kidney, lymph node, small intestine, pancreas, blood cells, bone, colon stomach, breast, endometrium, prostate, testicle, ovary, central nervous system, skin, head and neck, esophagus, and bone marrow cancer.

10. A method of claim 1, wherein the cancer is a hematological cancer.

11. A method of claim 1, wherein the cancer is selected from leukemia, lymphoma, multiple myeloma, myelodysplasia, myeloproliferative disease, refractory leukemia and promyelocytic leukemia.

12. A method of claim 1, wherein the compound and the one or more other therapeutic agents are administered simultaneously.

13. A method of claim 1, wherein the one or more other therapeutic agents are administered within about 5 minutes to within about 48 hours prior to or after administration of the compound.

14. A method of claim 13, wherein the one or more other therapeutic agents are administered within about 5 minutes to within about 1 hour prior to or after administration of the compound.

15. A kit comprising SGLU-1 and another therapeutic agent selected from bortezomib, melphalan, dexamethasone, irinotecan, oxaliplatin, 5-fluorouracil, doxorubicin, and sorafenib.

* * * * *